United States Patent
Hamamah et al.

(10) Patent No.: US 11,149,314 B2
(45) Date of Patent: Oct. 19, 2021

(54) METHODS FOR DETERMINING THE QUALITY OF AN EMBRYO

(71) Applicants: INSERM (INSTITUT NATIONAL DE LA SANTE ET DE LA RECHERCHE MEDICALE), Paris (FR); UNIVERSITE DE MONTPELLIER, Montpellier (FR); CENTRE HOSPITALIER UNIVERSITAIRE DE MONTPELLIER, Montpellier (FR); INSTITUT RÉGIONAL DU CANCER DE MONTPELLIER, Montpellier (FR)

(72) Inventors: Samir Hamamah, Montpellier (FR); Safia El Messaoudi, Montpellier (FR); Alain Thierry, Montpellier (FR); Said Assou, Montpellier (FR)

(73) Assignees: INSERM (Institut National de la Santé et de la Recherche Médicale), Paris (FR); Université de Montpellier, Montpellier (FR); Centre Hospitalier Universitaire de Montpellier, Montpellier (FR); Institut Régional du Cancer de Montpellier, Montpellier (FR)

( * ) Notice: Subject to any disclaimer, the term of this patent is extended or adjusted under 35 U.S.C. 154(b) by 0 days.

(21) Appl. No.: 16/135,293

(22) Filed: Sep. 19, 2018

(65) Prior Publication Data
US 2019/0002985 A1 Jan. 3, 2019

Related U.S. Application Data

(62) Division of application No. 14/898,591, filed as application No. PCT/EP2014/062895 on Jun. 18, 2014, now abandoned.

(30) Foreign Application Priority Data

Jun. 18, 2013 (EP) ..................................... 13305820

(51) Int. Cl.
*C12Q 1/6883* (2018.01)

(52) U.S. Cl.
CPC ..... *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2012/0016184 A1* 1/2012 Yao .................. G06F 19/00
600/33

FOREIGN PATENT DOCUMENTS

WO WO 2008/084105 * 7/2008

* cited by examiner

*Primary Examiner* — Katherine D Salmon
(74) *Attorney, Agent, or Firm* — W & C IP (57) ABSTRACT

The present invention relates generally to the fields of reproductive medicine. More specifically, the present invention relates to in vitro non invasive methods and kits for determining the quality of an embryo by determining the level of the cell free nucleic acids and/or determining the presence and/or expression level of at least one specific nucleic acid sequence in the nucleic acid extraction.

2 Claims, 7 Drawing Sheets
Specification includes a Sequence Listing.

METHODS FOR DETERMINING THE QUALITY OF AN EMBRYO

CROSS-REFERENCE TO RELATED APPLICATIONS

This application is a divisional of U.S. patent Publication Ser. No. 14/898,591, filed Dec. 15, 2015, which itself was a national stage filing of international application PCT/EP2014/062595 filed Jun. 18, 2014, and that international application claimed priority to European Application 13305820.6 filed Jun. 18, 2013.

FIELD OF THE INVENTION

The present invention relates generally to the fields of reproductive medicine. More specifically, the present invention relates to methods and kits for determining the quality of an embryo.

BACKGROUND OF THE INVENTION

Currently, there is no reliable commercially available genetic or non-genetic procedure for determining the quality of an embryo during assisted reproductive technology (ART). Notably an essential issue remains to determine whether an embryo is capable of yielding viable offspring when transferred to an appropriate uterine environment. Another important issue is to determine the genetic profiling of an embryo that will render the development of the fetus and even after of the child viable.

The selection of embryos with higher implantation potential is one of the major challenges in assisted reproductive technology (ART). Initially, multiple-embryo transfer (MET) was used to maximize pregnancy rates. However, improved embryo quality and raising multiple pregnancy rates have resulted in the decrease in the number of embryos for replacement. Therefore, selection of the 'best' embryo has become crucial, particularly with elective single embryo transfer (SET) being strongly recommended. There is therefore a need to develop new objective approaches for embryo selection. The classical methods to select healthy embryos under IVF and ICSI conditions are based on subjective morphological criteria such as fragmentation degree and the presence of multi-nucleation, the number and size of blastomeres, early embryonic cleavage (Ebner et al., 2003; Fenwick et al., 2002). However, most studies suggest that embryos with proper morphological appearance alone are not sufficient to predict a successful implantation. Considering the limitation of morphologic evaluation and cytogenetic screening methods, there is now a movement toward more sophisticated, high-performance technologies and the emerging 'omits' science, such as transcriptomics and metabolomics. These approaches focus on a variety of bodily cells as well as embryonic culture media. An indirect and attractive approach for predicting embryo and pregnancy outcomes has been reported by our team using transcriptomic data of cumulus cells (CCs) gene expression (Assou et al., 2011; Assou et al., 2008). We observed that there was no relationship between embryo morphological aspects and the CC gene expression profile (Assou et al., 2010). Other studies reported that metabolomic profile of spent culture media by Raman or near-infrared (NIR) spectroscopy correlates with reproductive potential of individual embryos (Self et al., 2007; Vergouw et al., 2008). They showed also that metabolomic profiling of culture media from embryos was independent of morphology.

Another major cause of reduced implantation rate is poor genetic quality of the implanted embryo. For example, most embryonic wastage and loss are caused by aneuploidies (chromosome number abnormalities) that are lethal and occur in approximately 60% of all spontaneous abortions and still births. Other genetic abnormalities include chromosomal aneuploidy, amplification, translocation, insertion/deletion, inversion, short tandem repeat polymorphisms, microsatellite polymorphisms, single nucleotide polymorphisms (SNPs), and other structural abnormalities. Genetic abnormalities can cause many phenotypic diseases and some are even lethal. If genetic abnormalities occur in embryos, many types of prenatal conditions and congenital diseases are likely to develop. Screening these abnormalities by preimplantation genetic diagnosis (PGD) is very important to ensure a structurally normal embryo selection and viable implantation. However, current methods are invasive may cause prejudice to the embryo.

It was reported that cell free DNA may be detected in biological fluids such as blood, ascite, urine, amniotic fluid, feces, saliva or cerebrospinal fluids. Various nucleic acids such as DNA, RNA, miRNA were indeed isolated and detected in cell free form. cfDNA was found detectable amount in healthy subjects as well as, in greater amount, in some pathological disorders (cancer, myocardial infarction, autoimmune disease, sepsis, trauma, . . . ) or specific physiological state (intense effort, . . . ). The mechanisms of release of cfDNA are very poorly known, but it has been suggested that necrosis, apoptosis, phagocytosis or active release might be implicated. CfDNA analysis is an area of active investigation in the diagnostic field especially in two areas is subjected to high scrutiny at this time. However, detection of cfDNA has not yet been investigated for determining the quality of an embryo.

SUMMARY OF THE INVENTION

The present invention is based on the dramatic discovery of the presence of amounts of cell free nucleic acids in the culture medium where the embryo is grown under in vitro fertilization conditions. The inventors demonstrate that the level of said cell free nucleic acids in the culture medium is informative about the ability of the embryo to give rise to a pregnancy. Moreover, the inventors demonstrate that the analysis of said cell free nucleic acids make the detection and expression of a specific sequence gene expression possible and pave the way for the development of a non-invasive method for the genetic profiling of an embryo.

DETAILED DESCRIPTION OF THE INVENTION

The present invention relates to an in vitro non invasive method for determining the quality of an embryo comprising the steps consisting of i) providing a sample of the culture medium where the embryo is grown, ii) extracting the cell free nucleic acids from the sample and iii) determining the level of the cell free nucleic acids in the nucleic acid extraction and/or determining the presence and/or expression level of at least one specific nucleic acid sequence in the nucleic acid extraction.

As used herein the term "embryo" has its general meaning in the art and refers to a fertilized oocyte or zygote. The term "embryo" also refers to cells in all stages of development from a fertilized oocyte or zygote up to the 5 or 6 days (blastocyst stage). Said fertilization may intervene under a classical in vitro fertilization (cIVF) conditions or under an intracytoplasmic sperm injection (ICSI) procedure. Examples of embryos that may be assessed by the methods of the invention include 1-cell embryos (also referred to as zygotes), 2-cells embryo, 3-cells embryo, 4-cells embryo, 5-cells embryo, 6-cells embryo, 8-cells embryo, etc. typically up to and including 16-cells embryo, any of which may be derived by any convenient manner, e.g. from an oocyte that has matured in vivo or from an oocyte that has matured in vitro. As used herein, the term "blastocyst" refers to the structure formed in the early embryogenesis of mammals, after the formation of the morula. It possesses an inner cell mass (ICM), or embryoblast, which subsequently forms the embryo, and an outer layer of cells, or trophoblast, which later forms the placenta. The trophoblast surrounds the inner cell mass and a fluid-filled blastocyst cavity known as the blastocoele. The human blastocyst comprises 70-100 cells. Blastocyst formation begins at day 5/6 after fertilization in humans.

According to the invention, the oocyte may result from a natural cycle, a modified natural cycle or a stimulated cycle for cIVF or ICSI. The term "natural cycle" refers to the natural cycle by which the female or woman produces an oocyte. The term "modified natural cycle" refers to the process by which, the female or woman produces an oocyte or two under a mild ovarian stimulation with GnRH antagonists associated with recombinant FSH or hMG. The term "stimulated cycle" refers to the process by which a female or a woman produces one or more oocytes under stimulation with GnRH agonists or antagonists associated with recombinant FSH or hMG.

The term "classical in vitro fertilization" or "cIVF" refers to a process by which oocytes are fertilised by sperm outside of the body, in vitro. IVF is a major treatment in infertility when in vivo conception has failed. The term "intracytoplasmic sperm injection" or "ICSI" refers to an in vitro fertilization procedure in which a single sperm is injected directly into an oocyte. This procedure is most commonly used to overcome male infertility factors, although it may also be used where oocytes cannot easily be penetrated by sperm, and occasionally as a method of in vitro fertilization, especially that associated with sperm donation.

By "determining the quality of an embryo" it is meant that the method of the invention aims at determining whether an embryo is competent and/or bears a genetic abnormality or a specific sequence in the context of in vitro fertilization. The method of the invention allows the assessment of the ability of an embryo to perform successfully either or both in terms of conferring a high pregnancy rate and/or resulting in a healthy person. Accordingly the method of the invention is able to combine pre-implantation genetic testing and selection of the best embryo that is able to give rise to pregnancy.

The term "competent embryo" refers to an embryo with a high implantation rate leading to pregnancy. The term "high implantation rate" means the potential of the embryo when transferred in uterus, to be implanted in the uterine environment and to give rise to a viable fetus, which in turn develops into a viable offspring absent of a procedure or event that terminates said pregnancy.

As used herein the term "genetic abnormality" refers to any event that can exist in the genome of an individual (i.e. an embryo) that can give rise to cause a phenotypic disease and lethality. Genetic abnormalities include but are not limited to aneuploidy, translocation, gene/locus amplification, insertions, deletions, reversions, short tandem repeat (STR) polymorphisms, microsatellite polymorphisms, single nucleotide polymorphisms (SNPs), single genetic mutations responsible for inherited diseases, or a combination thereof. In particular, any genetically transmissible disease may be detected according to the present method. For example genetic alteration can include known alterations in one or more of the genes: CFTR, Factor VIII (F8 gene), beta globin, hemochromatosis, G6PD, neurofibromatosis, GAPDH, beta amyloid, and pyruvate kinase. The sequences and common mutations (e.g., single nucleotide polymorphisms or SNPs) of the genes are known. Other genetic abnormalities may be detected, such as those involving a sequence which is deleted in a human chromosome, is moved in a translocation or inversion, or is duplicated in a chromosome duplication, wherein said sequence is characterized in a known genetic disorder in the fetal genetic material. For example chromosome aneuploidy, such as Down syndrome (or trisomy 21), Edwards syndrome (trisomy 18), Patau syndrome (trisomy 13), Turner Syndrome (45X0) Klinefelter's syndrome (a male with 2 X chromosomes), Prader-Willi syndrome, and DiGeorge syndrome. A listing of known genetic abnormalities may be found in the OMIM database (http://omim.org/).

The method of the invention is applicable preferably to women but in theory may be applicable to other mammals (e.g., primates, dogs, cats, pigs, cows, mouse . . . ).

As used herein the term "nucleic acid" has its general meaning in the art and refers to refers to a coding or non coding nucleic sequence. Nucleic acids include DNA (deoxyribonucleic acid) and RNA (ribonucleic acid). Example of nucleic acid thus include but are not limited to DNA, mRNA, tRNA, rRNA, tmRNA, miRNA, piRNA, snoRNA, and snRNA. According to the invention, the nucleic acid may originate form the nucleus of the embryo or for the mitochondrial compartment of the embryo. By "cell free nucleic acid" it is meant that the nucleic acid is released by the embryo and present in the culture medium wherein the embryo is grown after in vitro fertilization or intracytoplasmic sperm injection (ICSI).

In a particular embodiment, sample is prepared when the embryo has reached the blastocyst stage corresponding to day 5 or 6 of the embryo development. Any methods well known in the art may be used for preparing a sample of the culture medium where the embryo was grown after in vitro fertilization or intracytoplasmic sperm injection (ICSI). One essential feature of the invention is that the embryo remains viable during preparation of the sample. No lytic enzyme or chemical reagents-based lysis solution are used to maintain the integrity of the embryo. The method of the invention is a perfect non-invasive method and only relies to the fact that an embryo is capable to release nucleic acids in the culture medium by a mechanism not yet determined.

Any methods well known in the art may be used by the skilled artisan in the art for extracting the free cell nucleic acid from the prepared sample. For example, the method described in the example may be used.

In a particular embodiment the method of the invention comprises the steps consisting of i) determining the level of the nucleic acid in the nucleic acid extraction, ii) comparing the level determined at step i) with a reference value, and iii) concluding that the embryo is competent when the level determined at step i) is lower than the reference value.

Determination of the level of the nucleic acid can be performed by a variety of techniques well known in the art. In a particular embodiment, quantitative PCR may be performed for determining the level of DNA such as described in El Messaoudi et al., 2013; Mouliere et al., 2013; Thierry et al., 2013 and WO2012/028746. In particular, the determination of the level of the nucleic acid may be performed as described in the example.

In a particular embodiment, the reference value consists in the level of the nucleic acids determined in an embryo culture medium at day 3 of embryo development. Accordingly, the decrease of the level between day 3 of embryo development and day 5 or 6 (blastocyst stage) indicates that the embryo is competent In a particular embodiment, the reference value is a threshold value or a cut-off value that can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the nucleic acid levels (obtained according to the method of the invention) with a defined threshold value. In one embodiment of the present invention, the threshold value is derived from the nucleic acid levels (or ratio, or score) determined in an embryo culture mediums derived from one or more patients undergoing IVF or ISCI. Furthermore, retrospective measurement of the nucleic acid levels (or ratio, or scores) in properly banked historical embryo culture mediums of patients undergoing IVF or ISCI may be used in establishing these threshold values.

In a particular embodiment the method of the invention comprises the steps consisting of i) detecting at least one mutation in the nucleic extraction, and ii) concluding that the embryo bears a genetic abnormality when the mutation is detected.

Typical techniques for detecting a mutation in a nucleic acid in particular DNA or mRNA include but are not limited restriction fragment length polymorphism, hybridisation techniques, sequencing, exonuclease resistance, microsequencing, solid phase extension using ddNTPs, extension in solution using ddNTPs, oligonucleotide assays, methods for detecting single nucleotide polymorphism such as dynamic allele-specific hybridisation, ligation chain reaction, minisequencing, DNA "chips", allele-specific oligonucleotide hybridisation with single or dual-labelled probes merged with PCR or with molecular beacons, and others.

Typically, mutations are detected after amplification. For instance, the isolated RNA may be subjected to coupled reverse transcription and amplification, such as reverse transcription and amplification by polymerase chain reaction (RT-PCR), using specific oligonucleotide primers that are specific for a mutated site or that enable amplification of a region containing the mutated site. According to a first alternative, conditions for primer annealing may be chosen to ensure specific reverse transcription (where appropriate) and amplification; so that the appearance of an amplification product be a diagnostic of the presence of a particular mutation. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to identify a mutation.

In particular sequencing represents an ideal technique that can be used in the context of the present invention. The one skilled in the art is familiar with several methods for sequencing of polynucleotides. These include, but are not limited to, Sanger sequencing (also referred to as dideoxy sequencing) and various sequencing-by-synthesis (SBS) methods as reviewed by Metzger (Metzger M L 2005, Genome Research 1767), sequencing by hybridization, by ligation (for example, WO 2005/021786), by degradation (for example, U.S. Pat. Nos. 5,622,824 and 6,140,053), nanopore sequencing. Preferably in a multiplex assay deep sequencing is preferred. The term "deep sequencing" refers to a method of sequencing a plurality of nucleic acids in parallel. See e.g., Bentley et al, Nature 2008, 456:53-59. The leading commercially available platforms produced by Roche/454 (Margulies et al., 2005a), Illumina/Solexa (Bentley et al., 2008), Life/APG (SOLiD) (McKernan et al., 2009) and Pacific Biosciences (Eid et al., 2009) may be used for deep sequencing. For example, in the 454 method, the DNA to be sequenced is either fractionated and supplied with adaptors or segments of DNA can be PCR-amplified using primers containing the adaptors. The adaptors are nucleotide 25-mers required for binding to the DNA Capture Beads and for annealing the emulsion PCR Amplification Primers and the Sequencing Primer. The DNA fragments are made single stranded and are attached to DNA capture beads in a manner that allows only one DNA fragment to be attached to one bead. Next, the DNA containing beads are emulsified in a water-in-oil mixture resulting in microreactors containing just one bead. Within the microreactor, the fragment is PCR-amplified, resulting in a copy number of several million per bead. After PCR, the emulsion is broken and the beads are loaded onto a pico titer plate. Each well of the pico-titer plate can contain only one bead. Sequencing enzymes are added to the wells and nucleotides are flowed across the wells in a fixed order. The incorporation of a nucleotide results in the release of a pyrophosphate, which catalyzes a reaction leading to a chemiluminescent signal. This signal is recorded by a CCD camera and a software is used to translate the signals into a DNA sequence. In the illumina method (Bentley (2008)), single stranded, adaptor-supplied fragments are attached to an optically transparent surface and subjected to "bridge amplification". This procedure results in several million clusters, each containing copies of a unique DNA fragment. DNA polymerase, primers and four labeled reversible terminator nucleotides are added and the surface is imaged by laser fluorescence to determine the location and nature of the labels. Protecting groups are then removed and the process is repeated for several cycles. The SOLiD process (Shendure (2005)) is similar to 454 sequencing, DNA fragments are amplified on the surface of beads. Sequencing involves cycles of ligation and detection of labeled probes. Several other techniques for high-throughput sequencing are currently being developed. Examples of such are The Helicos system (Harris (2008)), Complete Genomics (Drmanac (2010)) and Pacific Biosciences (Lundquist (2008)). As this is an extremely rapidly developing technical field, the applicability to the present invention of high throughput sequencing methods will be obvious to a person skilled in the art.

In a particular embodiment the method of the invention comprises the steps consisting of i) determining the level of at least one specific nucleic acid sequence, ii) comparing the level determined at step i) with a reference value and iii) concluding that the embryo bears a genetic abnormality when the level determined at step i) is different from the reference value (i.e. lower or higher depending on the nucleic acid looked).

Determining the expression level of a nucleic acid (in particular a gene, miRNA, snRNA, and snoRNA) may be assessed by any of a wide variety of well-known methods. Typically the prepared nucleic acid can be used in hybridization or amplification assays that include, but are not limited to, Southern or Northern analyses, polymerase chain reaction analyses, such as quantitative PCR (TaqMan), and probes arrays such as GeneChip™ DNA Arrays (AFF YMETRIX). Advantageously, the analysis of the expression level of a nucleic acid involves the process of nucleic acid amplification, e.g., by RT-PCR (the experimental embodiment set forth in U.S. Pat. No. 4,683,202), ligase chain reaction (BARANY, Proc. Natl. Acad. Sci. USA, vol. 88, p: 189-193, 1991), self sustained sequence replication (GUATELLI et al., Proc. Natl. Acad. Sci. USA, vol. 57, p: 1874-1878, 1990), transcriptional amplification system (KWOH et al., 1989, Proc. Natl. Acad. Sci. USA, vol. 86, p: 1173-1177, 1989), Q-Beta Replicase (LIZARDI et al., Biol. Technology, vol. 6, p: 1197, 1988), rolling circle replication (U.S. Pat. No. 5,854,033) or any other nucleic acid amplification method, followed by the detection of the amplified molecules using techniques well known to those of skill in the art. Real-time quantitative or semi-quantitative RT-PCR is preferred. In a particular embodiment, the determination comprises hybridizing the sample with selective reagents such as probes or primers and thereby detecting the presence, or measuring the amount of the nucleic acid. Hybridization may be performed by any suitable device, such as a plate, microtiter dish, test tube, well, glass, column, and so forth. Nucleic acids exhibiting sequence complementarity or homology to the nucleic acid of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidity/biotin). The probes and primers are "specific" to the nucleic acid they hybridize to, i.e. they preferably hybridize under high stringency hybridization conditions (corresponding to the highest melting temperature -Tm-, e.g., 50% formamide, 5× or 6×SCC. 1×SCC is a 0.15 M NaCl, 0.015 M Na-citrate). Many quantification assays are commercially available from Qiagen (S.A. Courtaboeuf, France) or Applied Biosystems (Foster City, USA). Expression level of the nucleic acid may be expressed as absolute expression profile or normalized expression profile. Typically, expression profiles are normalized by correcting the absolute expression profile of the nucleic acid of interest by comparing its expression to the expression of a nucleic acid that is not a relevant, e.g., a housekeeping mRNA that is constitutively expressed. Suitable mRNA for normalization include housekeeping mRNAs such as the U6, U24, U48 and S18. This normalization allows the comparison of the expression profile in one sample, e.g., a patient sample, to another sample, or between samples from different sources.

Probe and or primers are typically labelled with a detectable molecule or substance, such as a fluorescent molecule, a radioactive molecule or any others labels known in the art. Labels are known in the art that generally provide (either directly or indirectly) a signal. The term "labelled" is intended to encompass direct labelling of the probe and primers by coupling (i.e., physically linking) a detectable substance as well as indirect labelling by reactivity with another reagent that is directly labeled. Examples of detectable substances include but are not limited to radioactive agents or a fluorophore (e.g. fluorescein isothiocyanate (FITC) or phycoerythrin (PE) or Indocyanine (Cy5)).

The reference value may be determined as above described and will depend on the nucleic acid for which the determination of the expression level is required for concluding that the embryo bears a genetic abnormality or a nucleic acid specific sequence.

The method of the invention is particularly suitable for reaching a clinical decision. As used herein the term "clinical decision" refers to any decision to take or not take an action that has an outcome that affects the health or survival of the embryo. In particular, in the context of the invention, a clinical decision refers to a decision to implant or not the embryo of in the uterus of the patient. A clinical decision may also refer to a decision to conduct further testing, to take actions to mitigate an undesirable phenotype, or to take actions to prepare for the birth of a child with abnormalities. In particular the method as above described will thus help embryologist to avoid the transfer in uterus of embryos with a poor potential for pregnancy outcome. The method as above described is also particularly suitable for avoiding multiple pregnancies by selecting the competent embryo able to lead to an implantation and a pregnancy and therefore fewer embryos could be transferred at each cycle, resulting in a decreased incidence of multiple pregnancies.

The methods of the invention are particularly suitable for enhancing the pregnancy outcome of a child with a minimum of risk of having a genetic abnormality. Accordingly the invention also relates to a method for enhancing the pregnancy outcome of a patient comprising the steps consisting of i) providing a plurality of embryos, ii) determining the quality of the embryo by the method according to the invention and iii) selecting the most competent embryo with the minimum risk of bearing a genetic abnormality, and iv) implanting the embryo selected at step iii) in the uterus of said patient.

The invention also relates to a kit for performing the methods as above described, wherein said kit comprises means for determining the level of the cell free nucleic and/or means for determining the expression level of at least one specific nucleic acid and/or means for detecting at least one mutation, one SNP or a specific sequence in the nucleic acid extraction. Typically, the kits include probes, primers macroarrays or microarrays as above described. For example, the kit may comprise a set of probes as above defined, and that may be pre-labelled. Alternatively, probes may be unlabelled and the ingredients for labelling may be included in the kit in separate containers. The kit may further comprise hybridization reagents or other suitably packaged reagents and materials needed for the particular hybridization protocol, including solid-phase matrices, if applicable, and standards. Alternatively the kit of the invention may comprise amplification primers (e.g. stem-loop primers) that may be pre-labelled or may contain an affinity purification or attachment moiety. The kit may further comprise amplification reagents and also other suitably packaged reagents and materials needed for the particular amplification protocol.

The invention will be further illustrated by the following figures and examples. However, these examples and figures should not be interpreted in any way as limiting the scope of the present invention.

EXAMPLE

Material & Methods

IVF Procedure

The women underwent a gonadotropin-releasing hormone (Gn-RH) long or antagonist protocols treatment, which was followed by ovarian stimulation by hMG (human menopausal gonadotropin) or recombinant follicle-stimulating hormone (FSH). When at least three follicles reached a mean diameter of 17 mm under transvaginal ultrasound examination, 5000 IU ECG was administrated. Then, 36 h later, the oocytes were retrieved by ultrasound-guided trans-vaginal puncture. Conventional IVF or ICSI was use as indicated. Fertilization was confirmed 16 to 20 h after oocyte insemination or microinjection by the presence of two distinct pronuclei under the inverted microscope+two ploar bodies. The zygotes were then placed individually into fresh 30 µl droplets of culture medium (G1.5, Vitolife, Sweden) covered with mineral oil and maintained in a tri-gas incubator, which provide a 5% oxygen environment. All embryos were cultured in individual droplets at all times. The embryos were placed into extended culture media and continued until day 5. G2.5 medium (Vitolife, Sweden) was used for extended culture.

Quantification of the cfDNA in Culture Media of the Invention

Embryo Culture Media Sampling

After the removal of the embryos, the culture media were placed individually into labeled cryovials and then labeled again with a randomly assigned accession number. The collected specimens were immediately frozen and stored at −80° C. A control sample incubated under the same conditions without an embryo was also collected. Up to 50 µL may be sampled from the culture media.

cDNA Extraction

For Day 3 or Day5/6 samples, initial volume of 30 µL was completed to 200 µL with 1704 of PBS 1X. For D5 samples, initial volume of 10 µL was completed to 200 µL with 190 µL of PBS 1X. Subsequently, samples were either immediately handled for DNA extraction. CcfDNA was extracted from 200 µL of the sample using the QIAmp DNA Mini Blood Kit (Qiagen, Hilden, Germany) according to the "Blood and body fluid protocol." DNA samples were kept at −20° C. until use.

cfDNA Quantification by Q-PCR

The methodology and the data description were carried out according to the MIQE guidelines.q-PCR amplifications were carried out at least in duplicate in a 25-µl reaction volume on a CFX 96™ real-time PCR detection system using the CFX manager™ software (Bio-Rad, Hercules, Calif.). Each PCR mixture was composed of 12.5 µl of PCR mix (Bio-Rad Supermix SYBR Green), 2.5 µl of each amplification primer (0.3 pmol/µl), 2.5 µl of PCR-analyzed water, and 5 µl of DNA extract. Thermal cycling consisted of three repeated steps: a 3-minute hot-start polymerase activation-denaturation step at 95° C. followed by 40 repeated cycles at 95° C. for 10 seconds and then at 60° C. for 30 seconds. Melting curves were obtained by increasing the temperature from 55 to 90° C. with a plate reading every 0.2° C. Serial dilutions of genomic DNA from human placenta cells (Sigma, Munich, Germany) were used as standard for quantification and their concentration and quality was assessed using a Qubit® 2.0 Fluorometer (Life Technologies). Every Q-PCR run comprised routine quality negative and positive controls. Each sample was analyzed in triplicate and each assay was repeated at least once. The cfDNA concentrations obtained were normalized to the precise concentration using the standard curve. The coefficient of variation of the concentration value due to cfDNA extraction and Q-PCR analysis was calculated as 24% from two experiments (n=12). Quantification of cfDNA in samples and realization of the standard curve were performed by using the primer systems described in Table 1 (KRAS B1 inv k Sense: SEQ ID NO: 1; and KRAS B2 inv k Antisense: SEQ ID NO:2). Concentration value determined by the test exhibit a coefficient of variation of 24%.

TABLE 1

Intplex primers used for cfDNA quantification.

| Species | Gene | Intplex Primer Name | Direction | Sequence 5'-3' | Tm (° C.) | Amplicon Size (bp) |
|---|---|---|---|---|---|---|
| Human | Kras | KRAS B1 inv k Sense | | CCTTGGGTTTCAAGTTATATG | 54.0 | 67 |
| Human | Kras | KRAS B2 inv k Antisense | | CCCTGACATACTCCCAAGGA | 59.4 | |

Primer Design

The sequences and characteristics of the selected primers are presented in Table 1. The primers were designed using the Primer 3 software and all sequences were checked for self-molecular or intermolecular annealing with nucleic acid folding software (mfold and oligoAnalyzer 1.2). We performed local alignment analyses with the BLAST program to confirm the specificity of the designed primers. Oligonucleotides were synthesized and purified on high performance liquid chromatography (HPLC) by Eurofins (Ebersberg, Germany) and quality control of the oligonucleotides was performed by matrix-assisted laser desorption ionization-time of flight (MALDI-TOF).

The Q-PCR system was designed to be able to quantify a sequence present in two copies of the human genome. It enables the highly specific and sensitive quantification of this sequence in one allele. Higher specificity is obtained by using Allele Specific with Blocker PCR with using the same primers (Mouliere, 2011). This method allows for distinguishing two sequences having only one nucleotide difference with a 0.005 mutant/WT ratio. Thus detecting and quantifying a specific sequence may correspond either at distinguishing a WT sequence versus sequences with a few nucleotides difference up to only one nucleotide difference such as in sequences with a point mutation or a SNP. Therefore the demonstration of the quantification of cfDNA in embryo culture medium as shown here, show the potential of this method to detect the presence of a single nucleotide mutation, SNP, or other genetic alterations.

Higher concentration values may be obtained when targeting repeated sequences in the nuclear genome such as the lyne sequence, or mitochondrial sequences.

Results

Detection of cfDNA in Embryo Culture Media

Figure 1:
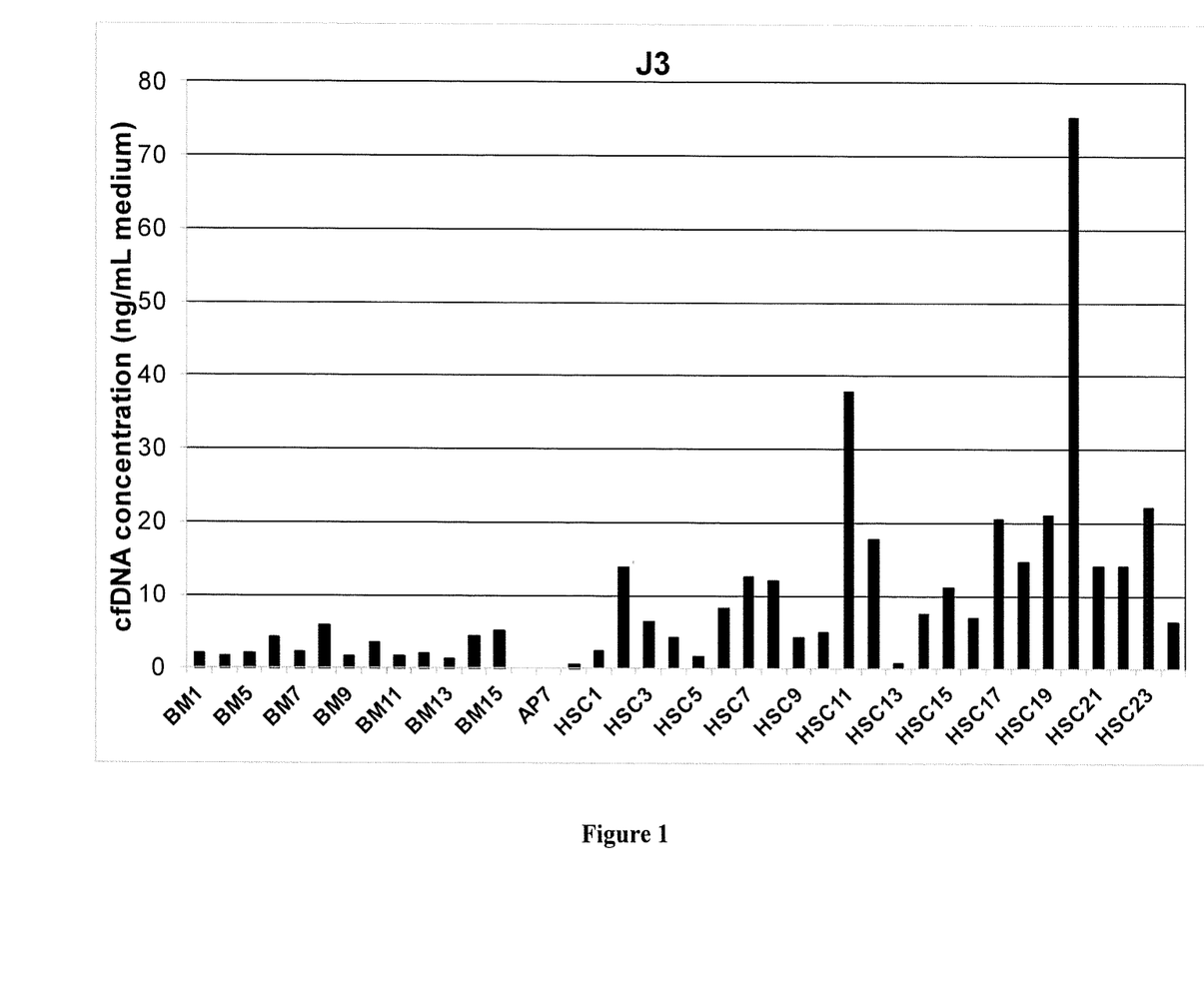
FIG. 1: cfDNA concentrations in culture medium of several embryos from two patients at Day3.
Figure 2:
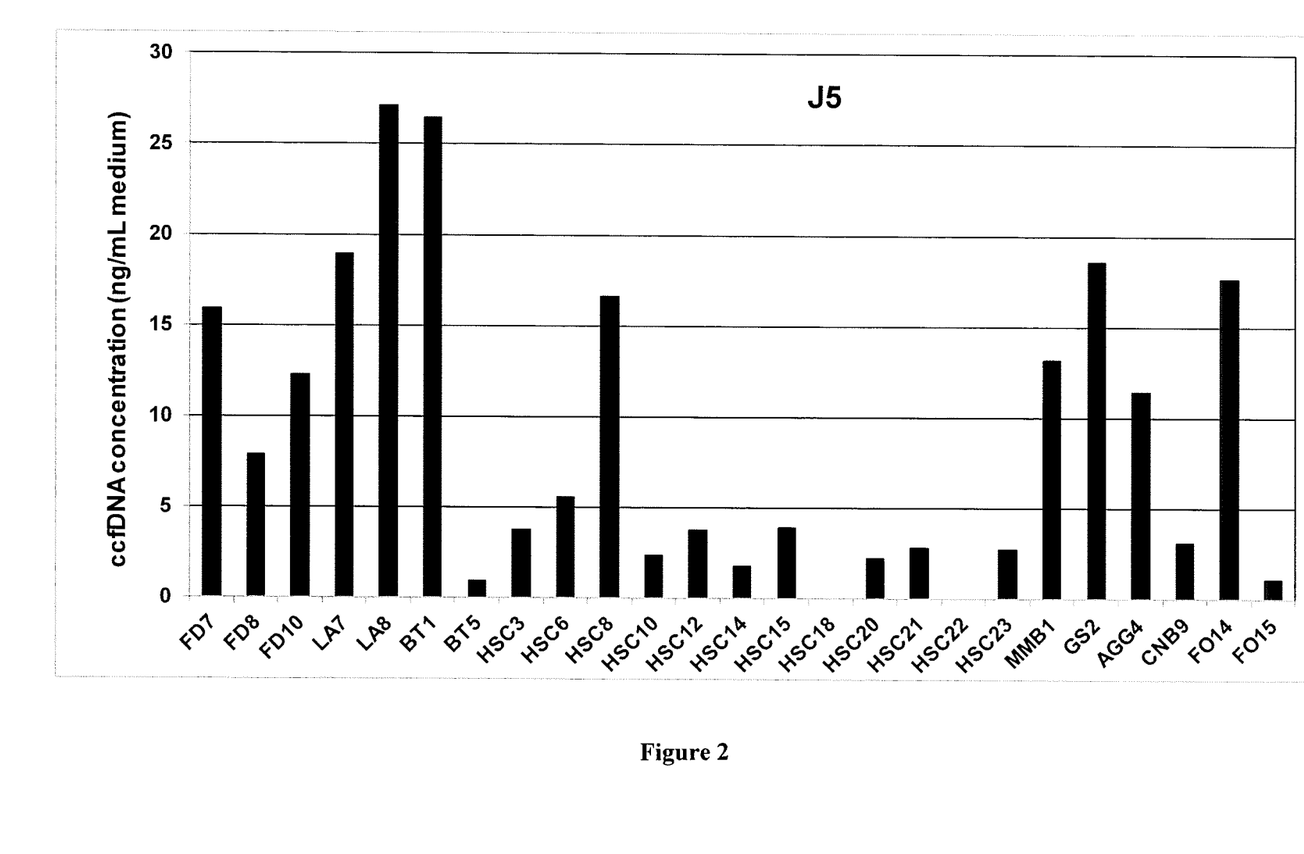
FIG. 2: cfDNA concentrations in culture medium of several embryos from 9 patients at Day5/6.

The targeted sequence has 2 copies per genome of the nucleus of diploid cell. CfDNA could significantly be detected in embryo culture media at D3 or D5/6 (FIG. 1). The test can detect down to 1.5 ng/ml medium and as such a minimum of 2 GE copy were found in culture medium. Up to of 27 ng/ml cfDNA or 36 GE was observed in D5/6 culture medium (FIG. 2). Note, those number may be relevant to the embryo development. As such this data reveals the possibility of the detection of the presence of a specific DNA sequence (at the most 2 copies per diploid cell) and therefore the potential presence of homozygous or heterozygous genetic or epigenetic alteration. CfDNA could significantly be detected in all samples and for each patient (FIG. 2).

Figure 3:
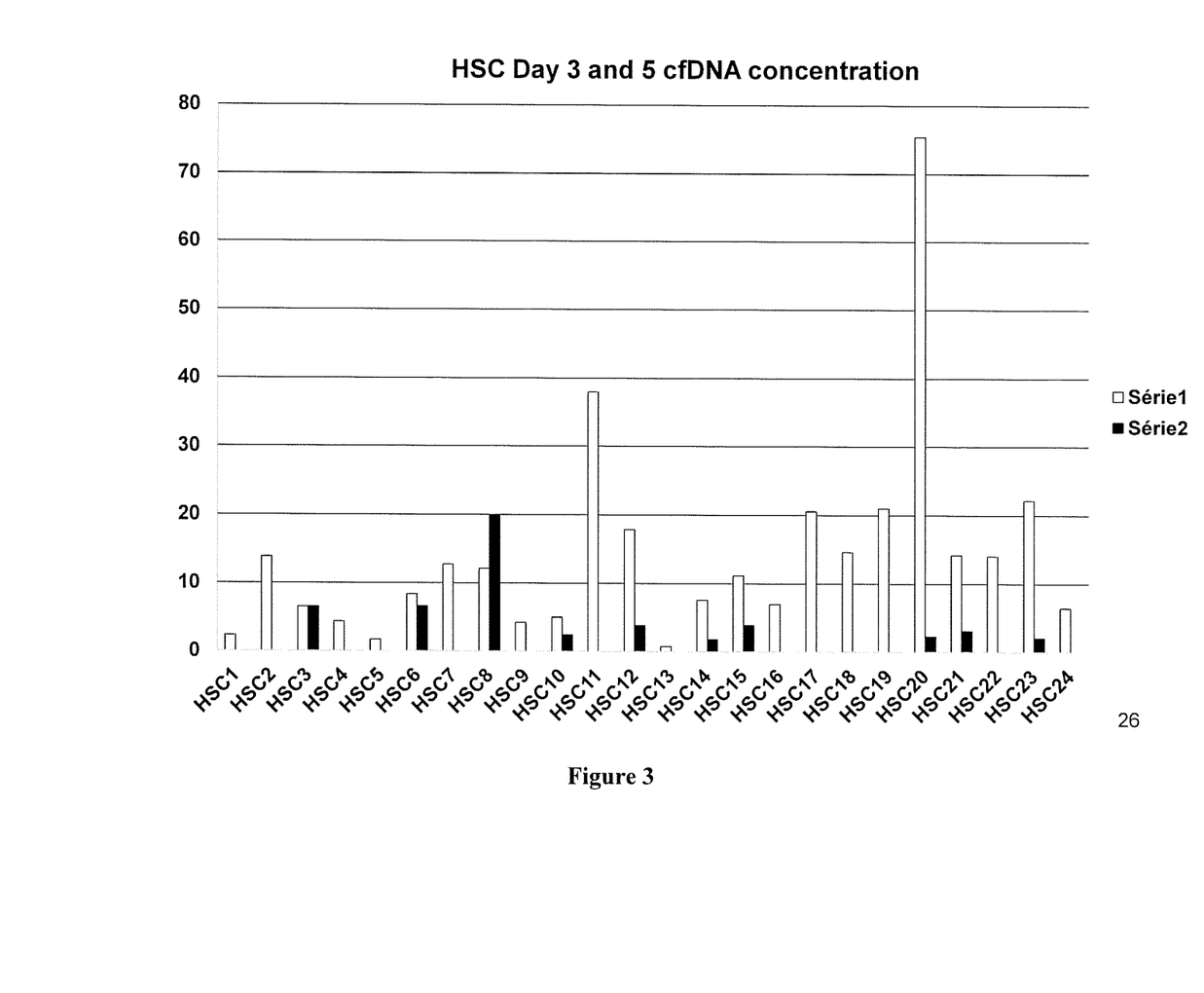
FIG. 3: cfDNA concentrations in culture medium of several embryos from two patients at Day3 and Day5. Dark histogram, D5/6 concentration. Clear histogram, D3 concentration.

There are significant (1 Log) intra and inter variation between samples buttressing the notion that dynamics of measurement enables comparison between samples (FIG. 3).

Relationship Between cfDNA and in vitro Embryo Outcome

Figure 4A:
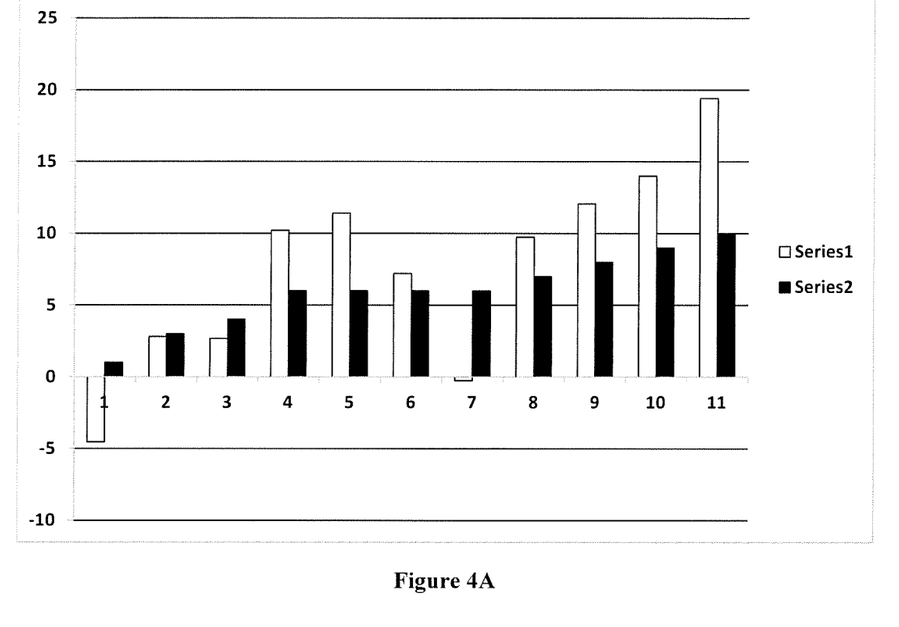
FIG. 4A: Difference of the cfDNA concentrations between Day3 and Day5/6 respective to embryo grade. Serie 1 histograms, D3-D5/6 concentration (ng/mL cfDNA); serie 2 histograms, ranking respective to growing grade (1-10). CfDNA concentration values obtained in the serie of the embryo of the HSC patient.
Figure 4B:
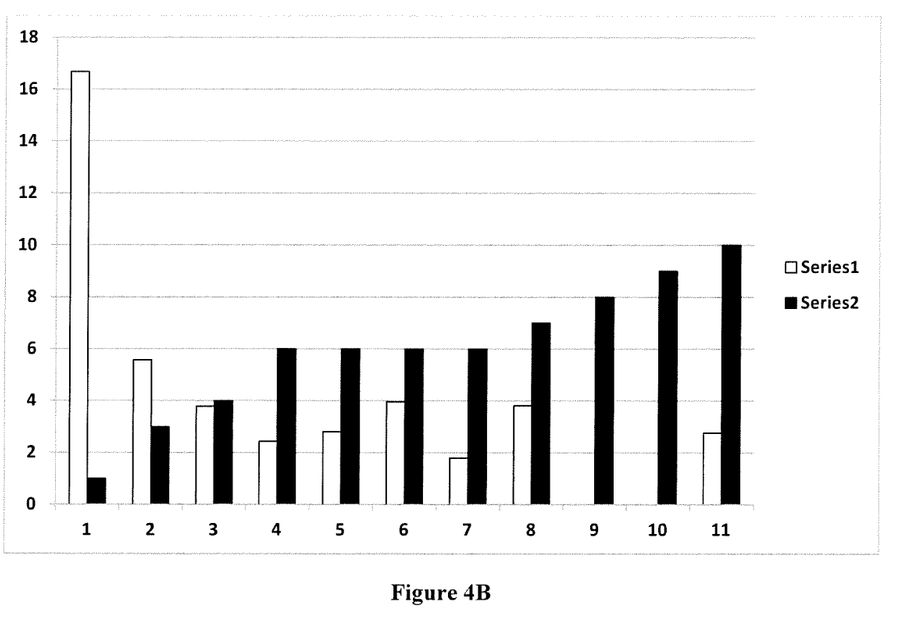
FIG. 4B: cfDNA concentrations respective to embryo grade. Serie 1 histograms, Day5/6 concentration (ng/mL cfDNA); serie 2 histograms, ranking respective to growing grade (1 to 10). CfDNA concentration values obtained in the serie of the embryo of the HSC patient.
Figure 5:
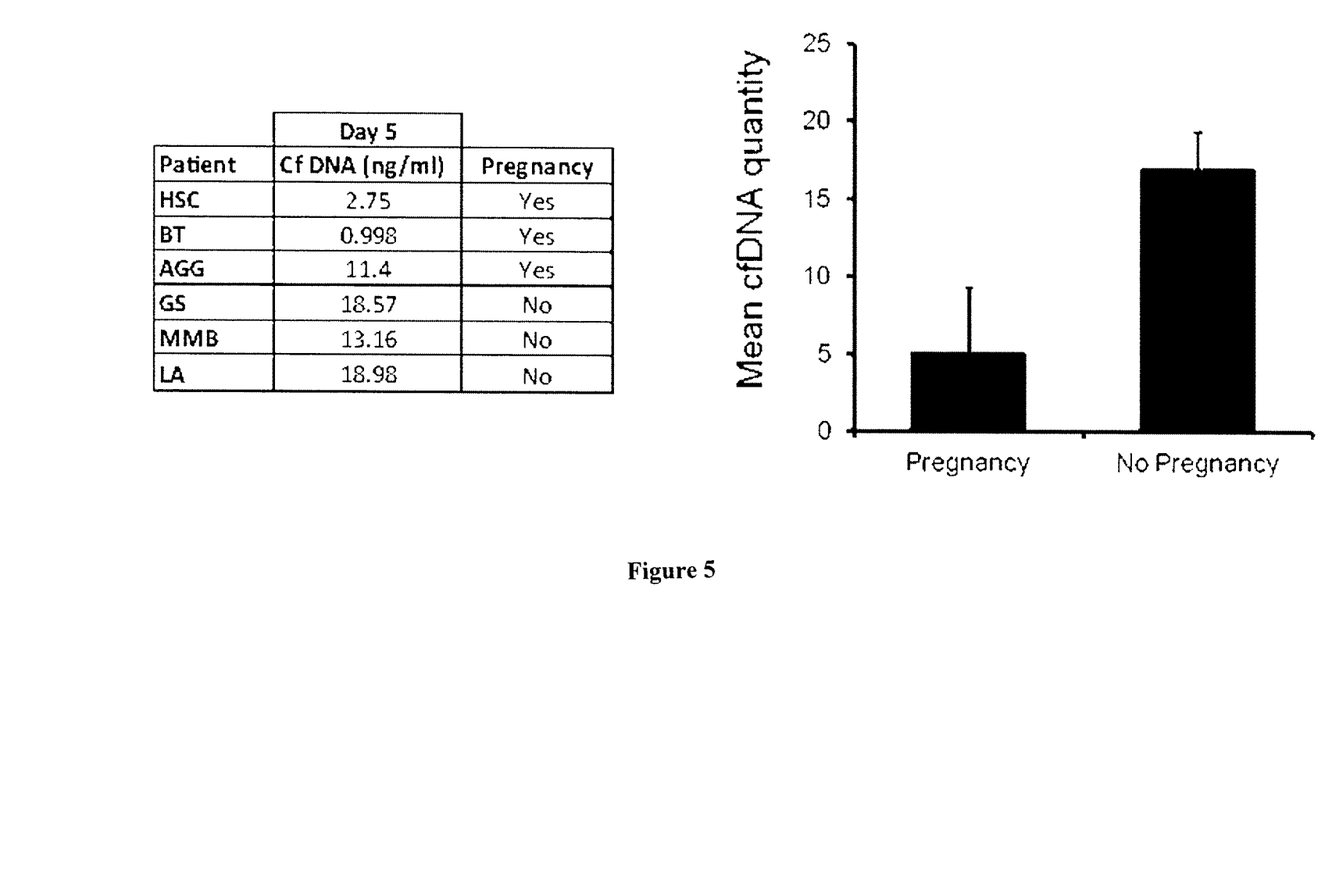
FIG. 5: Relationship between cfDNA in culture media and pregnancy outcome. Histograms comparing the mean cfDNA quantity in embryo culture media at day 5/6 issued from positive pregnancy patients and negative pregnancy patients.

The relation between cfDNA content of embryo culture medium and in vitro embryo development was also investigated:

cfDNA conc. determined at D3 and D5/6 could be compared in culture media of eleven embryos. As shown in (FIG. 4A), the values of the difference of the cfDNA concentration between D3 and D5/6 are growing respectively with the good embryo development as evaluated by morphological criteria. As presented in (FIG. 4B) cfDNA conc. values are inversely proportional to the good embryo development. Thus, both D5/6 cfDNA conc. and D3-D5/6 conc. decrease appear as a marker of in vitro embryo development.

cfDNA isolated from embryo culture media that developed into good quality 8-cells embryo at day 3 and leading to blastocyst stage at day 5/6 were selected and divided in three groups: i) cfDNA from embryo at day 3 that developed into good blastocyst quality at day 5/6 (grade 4AA, 4AB or 4BA, 5AA, 5AB or 5BA) and leading to pregnancy, (ii) cfDNA from embryo at day 3 developed into intermediary blastocyst quality at day 5/6 (grade 4BB or 5 BB), (iii) cfDNA from embryo at day 3 developed into bad blastocyst quality at day 5/6 (grade 4CC or 5CC) (see table 2 for patient HSC). The quantity of cfDNA in culture medium from embryo at day 3 that developed into good blastocyst quality at day 5/6 (grade 4AA,4AB, 4BA) and leading to pregnancy was 22.16 ng/ml and 2.75 ng/ml at day 3 and day 5/6 respectively (88%, decrease). The variation in the cfDNA value between day 3 and day 5/6 decreased to 7.55 ng/ml and 1.80 ng/ml (76%, decrease) in the intermediary grade and to 6.46 ng/ml (day 3) and 3.78 (days/6) (41%, decrease) in the no good blastocyst grade (Table 3). Interestingly, this variation is very low in the lyzed embryo 8.36 ng/ml (day 3) and 5.57 (day 5/6) (33%, decrease). Additionally, cfDNA quantities in embryo culture media at day 5/6 were evaluated according to patient outcome. We show that cfDNA were greater in embryo culture media at day 5/6 from no-pregnant patients than that of pregnant patients (FIG. 5).

cfDNA in Embryo Culture Medium Could be Used to Detect Male Embryos

Figure 6A:
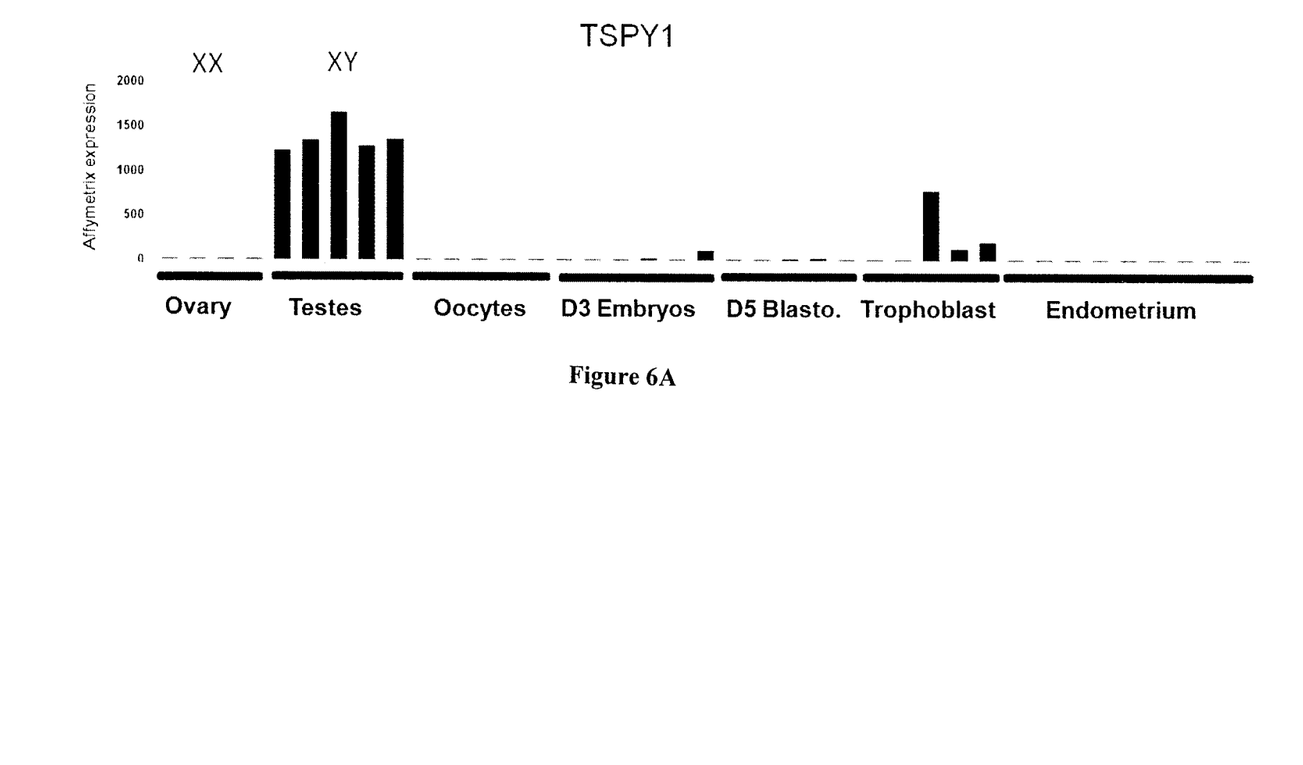
FIGS. 6A and 6B: Histograms show the microarray signal values for genes in ovary, testes, MII oocytes, day 3 embryos, day 5/6 blastocysts, trophectoderm and endometrium samples. Microarray data from MII oocytes, day 3 embryos, day 5/6 blastocysts, trophectoderm and endometrium samples were obtained from our team and those for ovary and testes samples were obtained from the Gene Expression Omnibus (GEO) through the provisional accession numbers (GPL570).
Figure 6B:
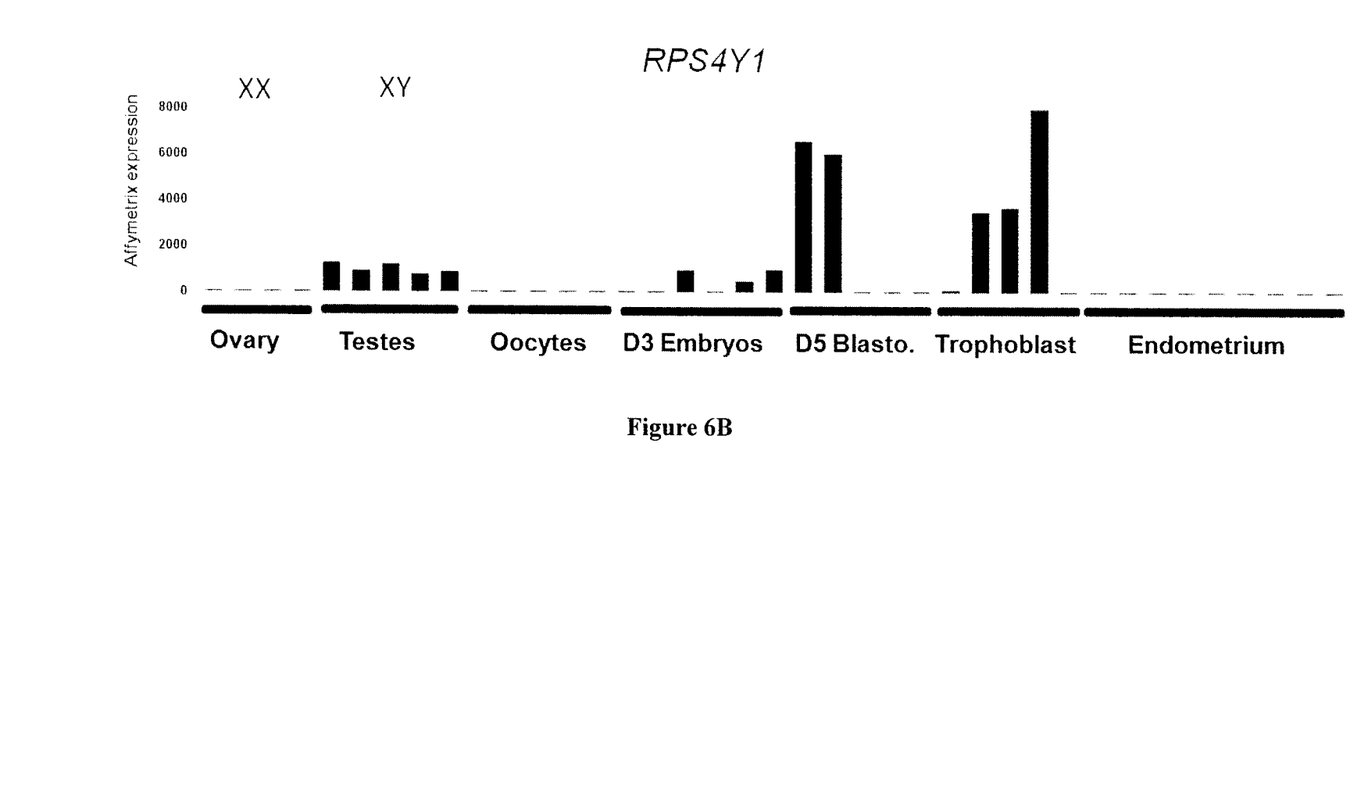

Genes such as TSPY1 (Testis specific protein, Y-linked 1) and RPS4Y1 (Ribosomal protein S4, Y-linked 1) could be used to revealed embryo sex. This opens up an appropriate strategy for screening embryos from couples known to be at risk for an X-linked disease. The high-density oligonucleotide Affymetrix HG-U133P microarray chips were used to investigate the expression of TSPY1 and RPS4Y1 in XX and XY samples. Our results reveal that TSPY1 and RPS4Y1 may prove valuable as biomarkers of embryo sex determination by amplifying the multicops of these genes (cfDNA) in the embryo culture medium (FIGS. 6A and 6B). The methods may be applicable to other genes localized on the chromosome Y: DDX3Y (DEAD (Asp-Glu-Ala-Asp) box polypeptide 3, Y-linked), EIFIAY (Eukaryotic translation) and Y chromosome gene (SRY).

TABLE 2

ICSI outcome of a patient (HSC) in relation to cfDNA detected in embryo culture media. Data generated from each mature MII oocyte (fertilization, embryo cleavage and blastocyst development) were recorded by an embryologist according to the morphological criteria of Gardner and Schoolcraft 1999.

| | | Day 2 | | | Day 3 | | |
|---|---|---|---|---|---|---|---|
| Patient (HSC) | Day 1 Fertilization | Blastomere number | Blastomere uniformity | % of fragmentatio | Blastomere number | Blastomere uniformity | % of fragmentatio |
| N°2 | Unfertilized | | | | | | |
| N°3 | fertilized | 4bl Equal. | Homo. | 10% | 7bl Equal. | Homo. | 15% |

TABLE 2-continued

ICSI outcome of a patient (HSC) in relation to cfDNA detected in
embryo culture media. Data generated from each mature MII oocyte (fertilization,
embryo cleavage and blastocyst development) were recorded by an embryologist
according to the morphological criteria of Gardner and Schoolcraft 1999.

| | | | | | | | |
|---|---|---|---|---|---|---|---|
| N°4 | fertilized | | 2PB | | | 2PB | |
| N° 5 | Unfertilized | | | | | | |
| N° 6 | fertilized | 4bl Unequal. | ±Homo. | 30% | 8bl Unequal. | Homo. | 40% |
| N°7 | fertilized | 4bl Equal. | Homo. | 10% | 8bl Equal. | Homo. | 30% |
| N°8 | fertilized | 4bl Equal. | ±Homo. | 5% | 8bl Equal. | Homo. | 15% |
| N°9 | Unfertilized | | | | | | |
| N°10 | fertilized | 4bl Equal. | Homo. | 10% | 8 bl Equal. | Homo. | 15% |
| N°11 | Unfertilized | | | | | | |
| N°12 | fertilized | 4bl Equal. | Homo. | 10% | 8bl Equal. | Heter. | 10% |
| N°13 | Unfertilized | | | | | | |
| N°14 | fertilized | 4bl Equal. | Homo. | 15% | 8bl Equal. | Homo. | 15% |
| N°15 | fertilized | 4bl Unequal. | Homo. | 15% | 6bl Unequal. | Heter. | 30% |
| N°16 | Unfertilized | | | | | | |
| N°17 | fertilized | 4bl Unequal. | ±Homo. | 20% | 10bl Unequal. | ±Homo. | 30% |
| N°18 | fertilized | 4bl Unequal. | ±Homo. | 15% | 9bl Unequal. | Heter. | 30% |
| N°19 | Unfertilized | | | | | | |
| N°20 | fertilized | 5bl Unequal. | ±Homo. | 10% | 8bl ± Equal. | Homo. | 15% |
| N°21 | fertilized | 3bl Equal. | Homo. | 30% | 8bl Unequal. | Homo. | 30% |
| N°22 | fertilized | 4bl Equal. | Homo. | 20% | 8bl ± Equal. | Homo. | 25% |
| N°23 | fertilized | 4bl Equal. | Homo. | 10% | 8bl ± Equal. | ±Homo. | 20% |
| N°24 | Unfertilized | | | | | | |

| Patient (HSC) | Day 5 Grade | Day 6 Grade | Pregnancy | Drop Day 3 Concentration CfDNA (ng/ml) | Drop Day 5 Concentration CfDNA (ng/ml) |
|---|---|---|---|---|---|
| N°2 | | | | 13.871 | |
| N°3 | | 3CC | | 6.46 | 3.787 |
| N°4 | | | | 2.938 | |
| N° 5 | | | | 4.73 | |
| N° 6 | | Lyzed | | 8.365 | 5.572 |
| N°7 | | 5BB (Frezing) | | 12.726 | |
| N°8 | STOP | | | 12.137 | 16.668 |
| N°9 | | | | 4.255 | |
| N°10 | B1 | other | | 12.653 | 2.435 |
| N°11 | | | | 33.647 | |
| N°12 | | 4AB (Frezing) | | 13.542 | 3.81 |
| N°13 | | | | 0.777 | |
| N°14 | B1+ | 5BB (Frezing) | | 7.55 | 1.804 |
| N°15 | B1 | 4BC (Stop) | | 11.167 | 3.955 |
| N°16 | | | | 6.923 | |
| N°17 | 3CC | 5CC (Stop) | | 20.515 | |
| N°18 | 4AC | 5BA (Frezing) | | 12.07 | N/A |
| N°19 | | | | 20.988 | |
| N°20 | B1 | 5BB (Frezing) | | 75.392 | 2.28 |
| N°21 | B1 | 5CC (Stop) | | 14.219 | 2.81 |
| N°22 | 3BB | 3BB (Frezing) | | 14.083 | N/A |
| N°23 | | AA (Transfer) | Positive | 22.168 | 2.755 |
| N°24 | | | | 6.41 | |

TABLE 3

Relationship between cfDNA in culture media and in vitro embryo
development. Three grades of blastocysts at day 5/6 (good (AA), intermediary (BB) or bad
quality (CC)) were obtained from good 8-cell embryos at day 3. The results indicate that the
cfDNA variation in culture media between day3 and day5/6 is different according to
blastocyst grade.

| | | Day 2 | | | Day 3 | | |
|---|---|---|---|---|---|---|---|
| Patient (HSC) | Day 1 Fertilization | Blastomere number | Blastomere uniformity | % of fragmentation | Blastomere number | Blastomere uniformity | % of fragmentation |
| N°23 | fertilized | 4 bl Equal. | Homo. | 10% | 8bl ± Equal. | ±Homo. | 20% |
| N°14 | fertilized | 4 bl Equal. | Homo. | 15% | 8bl Equal. | Homo. | 15% |
| N°3 | fertilized | 4 bl Equal. | Homo. | 10% | 7bl Equal. | Homo. | 15% |

| Patient (HSC) | Day 5 Grade | Day 6 Grade | Pregnancy | Drop Day 3 Concentration CfDNA (ng/ml) | Drop Day 5 Concentration CfDNA (ng/ml) |
|---|---|---|---|---|---|

TABLE 3-continued

Relationship between cfDNA in culture media and in vitro embryo development. Three grades of blastocysts at day 5/6 (good (AA), intermediary (BB) or bad quality (CC)) were obtained from good 8-cell embryos at day 3. The results indicate that the cfDNA variation in culture media between day3 and day5/6 is different according to blastocyst grade.

| N°23 | 5AA (Transfer) | | Positive | 22,168 | 2,755 |
| N°14 | B1+ | 5BB (Frezing) | | 7.55 | 1,804 |
| N°3 | | 3CC | | 6.46 | 3,787 |

REFERENCES

Throughout this application, various references describe the state of the art to which this invention pertains. The disclosures of these references are hereby incorporated by reference into the present disclosure.

Antonatos, D., Patsilinakos, S., Spanodimos, S., Korkonikitas, P. and Tsigas, D. (2006). Cell-free DNA levels as a prognostic marker in acute myocardial infarction. Ann N Y Acad Sci 1075, 278-81.

Arnalich, F., Maldifassi, M. C., Ciria, E., Quesada, A., Codoceo, R., Herruzo, R., Garcia-Cerrada, C., Montoya, F., Vazquez, J. J., Lopez-Collazo, E. et al. (2010). Association of cell-free plasma DNA with perioperative mortality in patients with suspected acute mesenteric ischemia. Clin Chim Acta 411, 1269-74.

Assou, S., Boumela, I., Haouzi, D., Anahory, T., Dechaud, H., De Vos, J. and Hamamah, S. (2011). Dynamic changes in gene expression during human early embryo development: from fundamental aspects to clinical applications. Hum Reprod Update 17, 272-90.

Assou, S., Haouzi, D., De Vos, J. and Hamamah, S. (2010). Human cumulus cells as biomarkers for embryo and pregnancy outcomes. Mol Hum Reprod 16, 531-8.

Assou, S., Haouzi, D., Mahmoud, K., Aouacheria, A., Guillemin, Y., Pantesco, V., Reme, T., Dechaud. H., De Vos, J. and Hamamah, S. (2008). A non-invasive test for assessing embryo potential by gene expression profiles of human cumulus cells: a proof of concept study. Mol Hum Reprod 14, 711-9.

Czamanski-Cohen, J., Sarid, O., Cwikel, J., Lunenfeld, E., Douvdevani, A., Levitas, E. and Har-Vardi, 1. (2013). Increased plasma cell-free DNA is associated with low pregnancy rates among women undergoing IVF-embryo transfer. Reprod Biomed Online 26, 36-41.

Destouni, A., Vrettou, C., Antonatos, D., Chouliaras, G., Traeger-Synodinos, J., Patsilinakos, S., Kitsiou-Tzeli, S., Tsigas, D. and Kanavakis. E. (2009). Cell-free DNA levels in acute myocardial infarction patients during hospitalization. Acta Cardiol 64, 51-7.

Ebner, T., Moser, M., Sommergruber, M., Gaiswinkler, U., Wiesinger, R., Puchner, M. and Tews, G. (2003). Presence, but not type or degree of extension, of a cytoplasmic halo has a significant influence on preimplantation development and implantation behaviour. Hum Reprod 18, 2406-12.

European patent PCT N°EP2011/065333 AR Thierry and F. Molina, Analytical methods for cell free nucleic acids and application, 5th of Sep. 2011.

Fenwick, J., Plattcau, P., Murdoch, A. P. and Herbert, M. (2002). Time from insemination to first cleavage predicts developmental competence of human preimplantation embryos in vitro. Hum Reprod 17, 407-12.

Goldshtein H, Hausmann M J, Douvdevani A. (2009). A rapid direct fluorescent assay for cell-free DNA quantification in biological fluids. Arm Clin Biochem. 46(Pt 6):488-94.

Lazar, L., Rigo, J., Jr., Nagy, B., Balogh, K., Mako, V., Cervenak, L., Mezes, M., Prohaszka, Z. and Molvarec, A. (2009). Relationship of circulating cell-free DNA levels to cell-free fetal DNA levels, clinical characteristics and laboratory parameters in preeclampsia. BMC Med Genet 10, 120.

Li C N, Hsu H L, Wu T L, Tsao K C, Sun C F, Wu J T. (2003). Cell-free DNA is released from tumor cells upon cell death: a study of tissue cultures of tumor cell lines. J Clin Lab Anal.17(4):103-7.

Mouliere, F., Robert B, Arnau Peyrotte E, Del Rio M, Yehou M, Molina F, Gongora C, Thierry A R. (2011). High Fragmentation Characterizes Tumour-Derived Circulating DNA. Plos One 6.

Mussolin, L., Burnetli, R., Pillon, M., Carraro, E., Farruggia, P., Todesco, A., Mascarin, M. and Rosolen, A. (2013). Plasma cell-free DNA in paediatric lymphomas. J Cancer 4, 323-9.

Schwarzenbach, H., Hoon, D. S. B. & Pantel, K. (2011). Cell-free nucleic acids as biomarkcrs in cancer patients. Nature Reviews Cancer 11, 426-437.

Seli, E., Sakkas, D., Scott, R., Kwok, S. C., Rosendahl, S. M. and Burns, D. H. (2007). Noninvasive metabolomic profiting of embryo culture media using Raman and near-infrared spectroscopy correlates with reproductive potential of embryos in women undergoing in vitro fertilization. Fertil Steril 88, 1350-7.

Thierry, A. R., Mouliere F, Gongora C, Ollier J, Robert B, Ychou M, Del Rio M, Molina F.(2010). Origin and quantification of circulating DNA in mice with human colorectal cancer xenografts. Nucleic Acids Res 38, 6159-6175.

Vergouw, C. G., Botros, L. L., Roos, P., Lens, J. W., Schats, R., Hompes, P. G., Burns, D. H. and Lambalk, C. B. (2008). Metabotomic profiling by near-infrared spectroscopy as a tool to assess embryo viability: a novel, non-invasive method for embryo selection. Hum Reprod 23, 1499-504.

Wroclawski, M. L., Serpa-Neto, A., Fonseca, F. L., Castro-Neves-Neto, O., Pompeo, A. S., Machado, M. T., Pompeo, A. C. and Del Giglio. A. (2013). Cell-free plasma DNA as biochemical biomarker for the diagnosis and follow-up of prostate cancer patients. Tumour Biol. May 29.

Yakimovich A, Gumpert H, Burckhardt C J, Lütschg V A, Jurgeit A, Sbalzarini I F, Greber U F. (2012). Cell-free transmission of human adenovirus by passive mass transfer in cell culture simulated in a computer model. J Virol. September; 86(18).

The invention claimed is:

1. A method for selecting a human embryo and subsequently implanting said embryo in a female undergoing in vitro fertilization, said method comprising the steps consisting of:
   i) providing a samples of the culture medium where the embryo is grown, said sample being prepared when the embryo has reached the blastocyst stage corresponding to day 5 or 6 of the embryo development;
   ii) extracting cell free nucleic acids from the sample;
   iii) determining the level of cell free nucleic acids in the nucleic acid extraction;
   iv) comparing the level determined at step iii) with the concentration of nucleic acids measured in a culture medium at day 3 of embryo development;
   v) selecting the embryo when the level determined at step iii) is lower than the concentration of nucleic acids measured in the culture medium at day 3 of embryo development; and
   vi) implanting the embryo selected in step v) in said female.

2. The method according to claim 1, wherein the step of determining the level of the cell free nucleic acids is performed by PCR or quantitative PCR.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Homo sapiens

<400> SEQUENCE: 1
ccttgggttt caagttatat g                                    21

<210> SEQ ID NO 2
<211> LENGTH: 20
<212> TYPE: DNA
<213> ORGANISM: Homo sapiens

<400> SEQUENCE: 2
ccctgacata ctcccaagga                                      20
```